US010460337B2

(12) United States Patent
Shum et al.

(10) Patent No.: US 10,460,337 B2
(45) Date of Patent: Oct. 29, 2019

(54) INTERACTIVE USE AND ATHLETIC PERFORMANCE MONITORING AND REWARD METHOD, SYSTEM, AND COMPUTER PROGRAM PRODUCT

(71) Applicant: NIKE, Inc., Beaverton, OR (US)

(72) Inventors: Albert Y. S. Shum, Portland, OR (US); Allan M. Schrock, Portland, OR (US)

(73) Assignee: NIKE, Inc., Beaverton, OR (US)

( * ) Notice: Subject to any disclaimer, the term of this patent is extended or adjusted under 35 U.S.C. 154(b) by 1041 days.

(21) Appl. No.: 14/449,640

(22) Filed: Aug. 1, 2014

(65) Prior Publication Data

US 2014/0344045 A1 Nov. 20, 2014

Related U.S. Application Data

(60) Continuation of application No. 10/431,331, filed on May 6, 2003, now Pat. No. 8,838,471, which is a
(Continued)

(51) Int. Cl.
*G06Q 30/00* (2012.01)
*G06Q 30/02* (2012.01)
(Continued)

(52) U.S. Cl.
CPC ....... *G06Q 30/0222* (2013.01); *A61B 5/0004* (2013.01); *A61B 5/0022* (2013.01);
(Continued)

(58) Field of Classification Search
CPC ......... G06Q 30/0207–30/0277; A63B 24/0062
(Continued)

(56) References Cited

U.S. PATENT DOCUMENTS 1,963,110 A 6/1934 Assael
3,797,010 A 3/1974 Adler et al.
(Continued)

FOREIGN PATENT DOCUMENTS

DE 3447171 A1 9/1985
EP 0908701 A2 4/1999
(Continued)

OTHER PUBLICATIONS

International Search Report in corresponding PCT application, application No. PCT/US2005/012954, dated Aug. 26, 2005.
(Continued)

*Primary Examiner* — Michael Bekerman
(74) *Attorney, Agent, or Firm* — Banner & Witcoff, Ltd.

(57) ABSTRACT

A method, computer program product, and system for monitoring and rewarding athletic performance and use of a product worn by a person, thereby motivating use of the product and promoting customer loyalty. The present invention includes and system and method for measuring, tracking, and recording use of the product, preferably related to the athletic performance of an athlete, using a portable, remote device; transferring that data from the remote device to a common location, such as an Internet web site service; calculating, assigning, and tracking rewards based on the level of use determined from the data; and allowing the user to redeem his or her rewards or compare his or her performance level with other athletes using other remote devices.

20 Claims, 3 Drawing Sheets

Related U.S. Application Data division of application No. 09/453,645, filed on Dec. 3, 1999, now Pat. No. 6,585,622.

(51) Int. Cl.

| | |
|---|---|
| *A63B 24/00* | (2006.01) |
| *A63B 71/06* | (2006.01) |
| *A61B 5/11* | (2006.01) |
| *A61B 5/00* | (2006.01) |
| *G01C 22/00* | (2006.01) |
| *G01P 3/00* | (2006.01) |
| *G06F 19/00* | (2018.01) |
| *A63B 69/00* | (2006.01) |
| *G16H 20/30* | (2018.01) |

(52) U.S. Cl.
CPC ............ *A61B 5/1118* (2013.01); *A61B 5/681* (2013.01); *A61B 5/6807* (2013.01); *A63B 24/0062* (2013.01); *A63B 24/0084* (2013.01); *A63B 71/06* (2013.01); *G01C 22/006* (2013.01); *G01P 3/00* (2013.01); *G06F 19/00* (2013.01); *G06Q 30/0207* (2013.01); *G06Q 30/0232* (2013.01); *G06Q 30/0233* (2013.01); *G06Q 30/0236* (2013.01); *A61B 2503/10* (2013.01); *A61B 2503/12* (2013.01); *A61B 2560/0475* (2013.01); *A61B 2560/0487* (2013.01); *A61B 2562/0219* (2013.01); *A63B 69/0028* (2013.01); *A63B 2071/0663* (2013.01); *A63B 2225/15* (2013.01); *A63B 2225/20* (2013.01); *A63B 2230/00* (2013.01); *G06F 19/3481* (2013.01); *G16H 20/30* (2018.01); *Y10S 482/90* (2013.01)

(58) Field of Classification Search
USPC .................................... 705/14.1–14.73; 482/8
See application file for complete search history.

(56) References Cited

U.S. PATENT DOCUMENTS

| | | | |
|---|---|---|---|
| 3,934,065 A | 1/1976 | Tung | |
| 4,104,102 A | 8/1978 | Eagon et al. | |
| 4,277,848 A | 7/1981 | Boehland | |
| 4,510,704 A | 4/1985 | Johnson | |
| 4,517,685 A | 5/1985 | Lesley | |
| 4,542,897 A | 9/1985 | Melton et al. | |
| 4,651,446 A * | 3/1987 | Yukawa ................ | A43B 3/00 235/105 |
| 4,716,458 A | 12/1987 | Heitzman et al. | |
| 4,743,971 A | 5/1988 | Hugli | |
| 4,752,764 A | 6/1988 | Peterson et al. | |
| 4,769,265 A | 9/1988 | Coburn, Jr. | |
| 4,771,394 A | 9/1988 | Cavanagh | |
| 4,808,471 A | 2/1989 | Grunzinger | |
| 4,828,257 A | 5/1989 | Dyer et al. | |
| 4,856,787 A | 8/1989 | Itkis | |
| 4,919,418 A | 4/1990 | Miller | |
| 4,925,189 A | 5/1990 | Braeunig | |
| 5,017,770 A | 5/1991 | Sigalov | |
| 5,089,960 A | 2/1992 | Sweeney, Jr. | |
| 5,203,848 A | 4/1993 | Wang | |
| 5,210,604 A | 5/1993 | Carpenter | |
| 5,213,555 A | 5/1993 | Hood et al. | |
| 5,235,416 A | 8/1993 | Stanhope | |
| 5,423,554 A | 6/1995 | Davis | |
| 5,456,648 A | 10/1995 | Edinburg et al. | |
| 5,466,200 A | 11/1995 | Ulrich et al. | |
| 5,524,637 A | 6/1996 | Erickson | |
| 5,547,439 A | 8/1996 | Rawls et al. | |
| 5,575,717 A | 11/1996 | Houriet, Jr. et al. | |
| 5,588,154 A | 12/1996 | Blauer et al. | |
| 5,594,469 A | 1/1997 | Freeman et al. | |
| 5,616,078 A | 4/1997 | Oh | |
| 5,626,537 A | 5/1997 | Danyo et al. | |
| 5,655,997 A | 8/1997 | Greenberg et al. | |
| 5,675,828 A | 10/1997 | Stoel et al. | |
| 5,720,200 A | 2/1998 | Anderson et al. | |
| 5,768,382 A | 6/1998 | Schneier et al. | |
| 5,785,632 A | 7/1998 | Greenberg et al. | |
| 5,794,267 A | 8/1998 | Wallace | |
| 5,864,333 A | 1/1999 | O'Heir | |
| 5,890,995 A | 4/1999 | Bobick et al. | |
| 5,890,997 A | 4/1999 | Roth | |
| 5,899,963 A | 5/1999 | Hutchings | |
| 5,913,727 A | 6/1999 | Ahdoot | |
| 5,916,063 A | 6/1999 | Alessandri | |
| 5,921,891 A | 7/1999 | Browne | |
| 5,941,797 A | 8/1999 | Kashiwaguchi | |
| 5,974,262 A | 10/1999 | Fuller et al. | |
| 5,982,352 A | 11/1999 | Pryor | |
| 5,989,157 A | 11/1999 | Walton | |
| 6,013,007 A * | 1/2000 | Root ................ | A63B 24/0006 482/8 |
| 6,018,705 A | 1/2000 | Gaudet et al. | |
| 6,024,675 A | 2/2000 | Kashiwaguchi | |
| 6,050,924 A | 4/2000 | Shea | |
| 6,066,075 A | 5/2000 | Poulton | |
| 6,077,193 A | 6/2000 | Buhler et al. | |
| 6,122,340 A | 9/2000 | Darley et al. | |
| 6,122,960 A | 9/2000 | Hutchings et al. | |
| 6,128,783 A | 10/2000 | Blauer et al. | |
| 6,175,960 B1 | 1/2001 | Knittel | |
| 6,191,773 B1 | 2/2001 | Maruno et al. | |
| 6,213,872 B1 | 4/2001 | Harada et al. | |
| 6,222,859 B1 | 4/2001 | Yoshikawa | |
| 6,231,527 B1 | 5/2001 | Sol | |
| 6,298,218 B1 | 10/2001 | Lowe et al. | |
| 6,298,314 B1 | 10/2001 | Blackadar et al. | |
| 6,405,381 B1 | 6/2002 | Bowman, Jr. | |
| 6,475,115 B1 | 11/2002 | Candito et al. | |
| 6,539,336 B1 | 3/2003 | Vock et al. | |
| 6,545,705 B1 | 4/2003 | Sigel et al. | |
| 6,572,511 B1 | 6/2003 | Volpe | |
| 6,585,622 B1 | 7/2003 | Shum et al. | |
| 6,595,858 B1 | 7/2003 | Tajiri et al. | |
| 6,605,038 B1 | 8/2003 | Teller et al. | |
| 6,669,600 B2 | 12/2003 | Warner | |
| 6,720,949 B1 | 4/2004 | Pryor et al. | |
| 6,898,550 B1 * | 5/2005 | Blackadar ............ | A43B 3/0005 702/182 |
| 7,106,360 B1 | 9/2006 | Frederick | |
| 7,789,800 B1 | 9/2010 | Watterson et al. | |
| 8,206,219 B2 | 6/2012 | Shum et al. | |
| 9,162,142 B2 | 10/2015 | Shum et al. | |
| 9,517,406 B2 | 12/2016 | Shum et al. | |
| 9,597,598 B2 | 3/2017 | Shum et al. | |
| 2002/0019258 A1 | 2/2002 | Kim et al. | |
| 2002/0019296 A1 | 2/2002 | Freeman et al. | |
| 2002/0036617 A1 | 3/2002 | Pryor | |
| 2002/0077219 A1 | 6/2002 | Cohen et al. | |
| 2002/0083507 A1 | 7/2002 | Mullis | |
| 2002/0097247 A1 | 7/2002 | Ohba | |
| 2002/0160883 A1 | 10/2002 | Dugan | |
| 2002/0176575 A1 | 11/2002 | Qawami et al. | |
| 2003/0008714 A1 | 1/2003 | Tajiri et al. | |
| 2003/0016368 A1 | 1/2003 | Aman et al. | |
| 2003/0031062 A1 | 2/2003 | Tsurugai et al. | |
| 2003/0050537 A1 | 3/2003 | Wessel | |
| 2003/0063115 A1 | 4/2003 | Kaku et al. | |
| 2004/0017473 A1 | 1/2004 | Marks | |
| 2004/0063480 A1 | 4/2004 | Wang | |
| 2004/0127334 A1 | 7/2004 | Heppert | |
| 2004/0127336 A1 | 7/2004 | Lapcevic | |
| 2010/0044588 A1 | 2/2010 | Park | |

FOREIGN PATENT DOCUMENTS

| | | |
|---|---|---|
| JP | 63186711 | 11/1988 |
| JP | 04-127674 B2 | 4/1992 |
| JP | 05-161724 | 6/1993 |
| JP | 07-185131 | 7/1995 |

(56) References Cited

FOREIGN PATENT DOCUMENTS

| JP | H08131654 A | 5/1996 |
|---|---|---|
| JP | H09248282 A | 9/1997 |
| JP | 2000-033184 | 2/2000 |
| JP | 2001129240 A | 5/2001 |
| JP | 2001155121 A | 6/2001 |
| JP | 2002500768 A | 1/2002 |
| JP | 2002519754 A | 7/2002 |
| JP | 2002-530970 | 9/2002 |
| JP | 2003221712 A | 8/2003 |
| JP | 2003316905 A | 11/2003 |
| JP | 2003333578 A | 11/2003 |
| JP | 2004264244 A | 9/2004 |
| JP | 2004313407 A | 11/2004 |
| JP | 2006077382 A | 3/2006 |
| JP | 2006086487 A | 3/2006 |
| WO | 9634310 A1 | 10/1996 |
| WO | 1999067702 A1 | 12/1999 |
| WO | 0031560 A2 | 6/2000 |
| WO | 0171397 A1 | 9/2001 |
| WO | 2005002436 A1 | 1/2005 |

OTHER PUBLICATIONS

Printout of Web page (Netpulse Frequent Fitness Program), dated Dec. 3, 1999, 3 pgs.
Printout of Web page from Interactive Fitness Technologies, Inc. (UltraCoach Standard), dated Nov. 30, 1999, 3 pgs.
Printout of Web page from Interactive Fitness Technologies. Inc. (UltraCoach Multi-Sport Training Software Products Catalog), dated Sep. 1999, 12 pgs.
Printout of Web page from Interactive Fitness Technologies, Inc. (UltraCoach VR: How it Works?), dated Nov. 30, 1999, 2 pgs.
Printout of Web page from Interactive Fitness Technologies, Inc. (UltraCoach VR Features), dated Nov. 30, 1999, 3 pgs.
Printout of Web page from Interactive Fitness Technologies, Inc. (UltraCoach Fit Software Comparisons), dated Nov. 30, 1999, 2 pgs.
Printout of Web page from Interactive Fitness Technologies, Inc. (UltraCoach Home Page), dated Nov. 30, 1999, 2 pgs.
Health Care. High-Tech Style. by Bernard Wyskockl, Jr:, The Well Street Journal, Apr. 17, 2001, 2 pgs.
Extended Search Report related in European Patent Application No. 09150346.6; dated Jan. 2, 2012.
Extended Search Report from European Patent Application No. 10178921.2; dated May 27, 2011.
Guskov, I., "Efficient Tracking of Regular Patterns on Non-rigid Geometry", University of Michigan, 2002: 1057-1060.
Extended Search Report from related European Patent Application No. 10150066.8; dated May 31, 2011.
International Search Report in corresponding 2004 PCT aplication, application No. PCT/US2003/34286, dated Jun. 2, 2004.
European Search Report in related European Application No. 10179570.6; dated Jul. 24, 2012.

* cited by examiner

INTERACTIVE USE AND ATHLETIC PERFORMANCE MONITORING AND REWARD METHOD, SYSTEM, AND COMPUTER PROGRAM PRODUCT

CROSS REFERENCE TO RELATED APPLICATION(S)

This application is a continuation of and claims priority to U.S. patent application Ser. No. 10/431,331 filed May 6, 2003, which is a division of U.S. patent application Ser. No. 09/453,645 filed Dec. 3, 1999, now U.S. Pat. No. 6,585,622 issued Jul. 1, 2003, the disclosures of which are hereby incorporated by reference in their entireties.

FIELD OF THE INVENTION

This invention relates to a method, computer program, and system for monitoring and rewarding use of a product, which is preferably an athletic product such as an article of footwear, thereby promoting customer loyalty and motivating people to use the product. In particular, the present invention includes a system and a method for measuring, tracking, and recording the athletic performance of an athlete using a remote device; transferring that data from the remote device to a common location, such as an Internet web site server; calculating, assigning, and tracking rewards based on the level of athletic performance determined from the data; and allowing the athlete to benefit from his or her earned rewards or compare his or her performance level with other athletes using other remote devices.

BACKGROUND OF THE INVENTION

Motivating people to exercise regularly is often a difficult task. Many forms of exercise, such as running and stair climbing, can be tedious, repetitive activities. Accordingly, some people tend to become bored with the activity over time and often give up before seeing meaningful results from their increased activity level.

Known devices for attempting to motivate people to exercise include devices for monitoring and recording key parameters such as heart rate, distance traveled and calories burned while the athlete is performing the athletic activity. For example, U.S. Pat. No. 5,899,963 to Hutchings, the disclosure of which is hereby incorporated by reference, discloses a device that measure the distance traveled, speed, and height jumped of a person wearing the device. This information may be stored and recalled on demand. An athlete may then use this information to track and monitor his progress, thereby motivating the athlete to exercise. However, these devices do not provide any method or system for allowing the athlete to earn redeemable rewards based on the level of activity recorded.

Similarly, enhanced visual displays and computer graphics have been used to motivate athletes to exercise. Typically, these displays include a virtual image of an athletic event, such as a running course. As an athlete runs on a treadmill, the displayed computer image simulates running along the race course. More sophisticated versions of these devices allow the runner to track and monitor athletic performance, "race" virtual runners, or even "race" other athletes using the similarly equipped devices on other treadmills. Data collecting devices, used to control the virtual images, are secured directly to the exercise equipment, such as the treadmill. Accordingly, if an athlete wishes to use these devices with a variety of equipment, separate data collecting devices must be purchased and used. Moreover, these equipment-mounted devices do not allow athletes to tract their athletic performance during activities unrelated to using that equipment. For example, an owner of such equipment could not monitor his or her athletic performance associated with playing a game of basketball, nor would this type of equipment motivate the athlete to do so.

On the other hand, some retailers have learned that rewarding customers for purchasing their goods or services motivates the customers to provide repeat business. Historically, for example, retailers have issued a specific number of stamps, known as "green stamps," to their customer for a given amount of purchases. The customer collects these stamps and may eventually redeem them for merchandise after collecting enough of them.

More recently, airlines have rewarded their passengers with frequent flyer miles for purchased tickets. By allowing the customers to exchange these miles for free or reduced fare airline travel, the airlines motivate their passengers to remain loyal to their services, and in some cases even to fly more frequently.

These award programs have extended into awarding frequent flying miles for qualifying goods purchased However, while these programs may encourage the initial purchase of the goods, they do not offer additional rewards when the purchaser actually uses the purchased goods. For example, under some frequent flying plans, a customer may be able to receive frequently flyer miles for purchasing a treadmill or running shoes. This is usually accomplished by the consumer paying for the purchase with a credit card that has been issued by the airline offering the reward. However, the purchaser does not receive any additional rewards for actually using the treadmill or running shoes purchased. Accordingly, these types of reward programs offer little incentive for an athlete to actually use athletic products purchased under these programs.

Thus, despite the known prior art methods and techniques, there remains a need for a method or system that encourages the actual use of a product. There also remains the need for a method or system that encourages persons to exercise.

SUMMARY OF THE INVENTION

In one or more embodiments of the present invention, it is therefore an object of the invention to provide a technique for encouraging exercising persons, including athletic and fitness product users, and sports participants (hereafter referred to as "athletes") to continue or increase their level of exercise. It is a further object of the invention to provide a technique for encouraging customers to actually use a purchased good worn by the person. It is still another object of the invention to provide a technique for encouraging an athlete to exercise by encouraging his use of athletic equipment, such as athletic shoes. These and other objects of the invention shall become apparent from the foregoing disclosure and claims.

According to one embodiment of the invention, a reward determination location, such as an athletic shoe manufacturer, collects product use information from a plurality of remote product use information gathering devices. Each remote product use information gathering device is associated with a product. The reward determination location then determines product use information from the collected product use information.

With another embodiment according to the invention, a reward determination location, such as an athletic shoe manufacturer, collects athletic performance information for a plurality of persons from a plurality of remote athletic performance measurement devices. The reward determination location then determines a reward for each of the plurality of persons from the collected athletic performance information.

For still another embodiment of the invention, a product user operates a product use information gathering device to measure information regarding use of a product. The product user then operates the information gathering device to transmit the gathered product use information to a reward determination location. In return, the product user receives information.

According to still yet another embodiment of the invention, an athlete operates a remote athletic performance measurement device to gather information relating to his athletic performance. The athlete then performs an athletic activity. After the athletic activity is completed, the athlete operates the athletic performance measurement device to transmit the gathered athletic performance information to a reward determination location. The athlete then receives reward information in response to the transmitted athletic performance information.

DETAILED DESCRIPTION

The present invention is directed to a method and system for monitoring athletic performance and rewarding that performance to thereby motivate the athlete.

Summary

Figure 1:
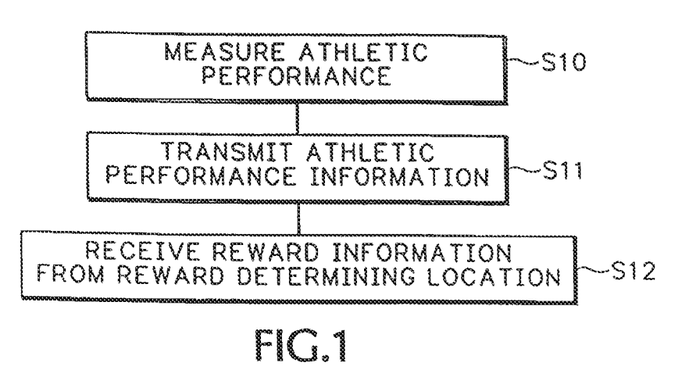
FIG. 1 is a block diagram of a method for encouraging athletic activity according for an exemplary embodiment of the present invention.

One preferred embodiment of the invention is shown in FIG. 1. According to this embodiment, an athlete taking advantage of the method of the invention measures his athletic performance over a period of time in step S10. As will be explained in detail below, the athlete can employ one or more of a variety of athletic performance measuring devices to gather information relating to his athletic performance.

At the end of the period, in step S11, the athlete transmits the gathered information to a reward determining location, such as an athletic equipment manufacturer. The athletic equipment manufacturer reviews the athletic performance information, and determines a reward for the athlete in proportion to his measured athletic performance. The manufacturer then transmits information relating to the reward back to the athlete. The athlete receives the reward information in step S12.

Figure 2:
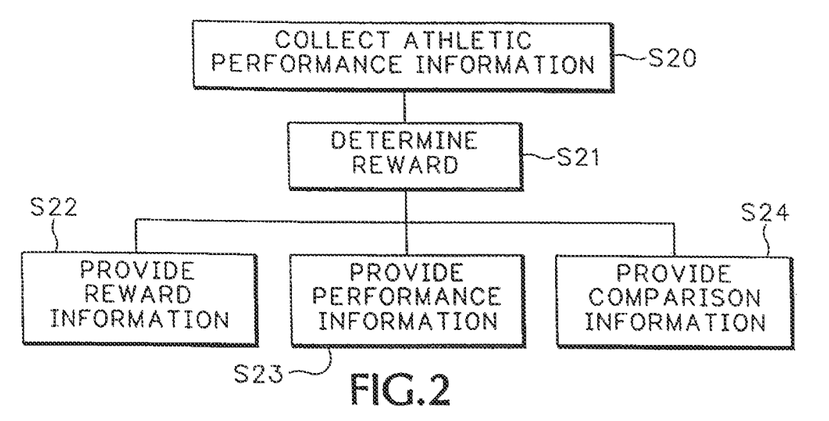
FIG. 2 is a block diagram of a method for encouraging athletic activity according to an alternative preferred exemplary embodiment of the present invention.

In a related embodiment of the invention, shown in FIG. 2, a reward determining location, such as an athletic equipment manufacturer, collects athletic performance information from a plurality of athletic performance measurement devices in step S20. As will be explained in detail below, each remote athletic performance measurement device gathers athletic performance information for one or more athletes, and transmits the information to the manufacturer. In step S21, the manufacturer then determines rewards for each athlete that are proportional to his measured athletic performance.

In addition to steps S20 and S21 noted above, alternate embodiments of the invention can include one or more of optional steps S22-S24. With optional step S22, the manufacturer transmits information relating to the determined reward back to the athlete. This direct feedback provides immediate positive reinforcement for the athletic activity.

The manufacturer also can provide performance information from an athlete to an authorized requestor, as shown in optional step S23. This step can be useful to, for example, the athlete's trainer, doctor, or another athlete. Further, because the manufacturer collects performance information from a number of athletes, the manufacturer can also prepare information comparing the performance of two or more athletes. The manufacturer can then provide this comparison information to an authorized requestor, as shown in optional step S24.

The various aspects of the invention will now be discussed in further detail, with reference to the attached drawings.

Gathering Performance Information

Figure 3:
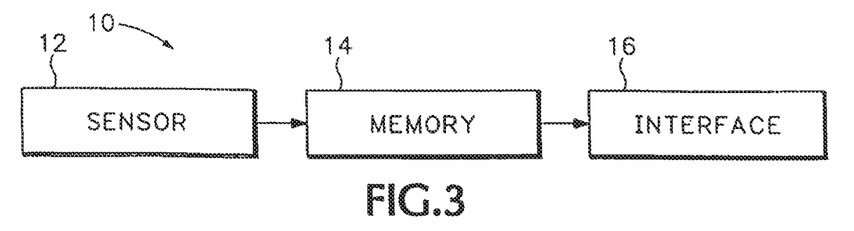
FIG. 3 is a block diagram showing one embodiment of an athletic performance measurement device according to the present invention.

As noted above, athletic performance information can be gathered by a variety of different athletic performance measurement devices. Preferably, the measurement devices 10 are light weight, portable, and attached to the athlete or articles worn by the athlete while exercising. One basic preferred athletic performance measurement device 10 is shown in FIG. 3. As seen in this figure, the athletic performance measurement device includes a sensor 12, a memory 14, and an interface 16.

The sensor 12 can be selected to measure any one of a variety of athletic performance values. According to one preferred embodiment, the athletic performance measurement device 10 is embedded in the sole of a shoe. With this embodiment, the sensor 12 is preferably an impact sensor that produces a pulse each time the shoe impacts the ground. Thus, the sensor 12 counts each step taken by the athlete. In an alternate embodiment, the sensor 12 is an accelerometer for detecting acceleration of the shoe. The construction and use of these types of sensors are well known in the art. See, for example, U.S. Pat. No. 5,899,963 to Hutchings.

The memory 14 of the device stores the measured performance information detected by the sensor 12 until the information is to be transmitted to the reward determination location 30, e.g., the shoe's manufacturer. When the athletic performance measurement device 10 transmits the stored performance information to the manufacturer, it transmits the information via the interface. For the embodiment of the invention with athletic performance measurement device 10 embedded in the sole of a shoe, the interface 16 is preferably a simple one. For example, the interface 16 can be a passive radio frequency transmitter. As is well known in the art, such transmitters can be "read" by exposing them to a radio frequency signal. The signal provides the transmitter with enough energy to transmit a reply signal containing the athletic performance information stored in the memory 14.

Figure 4:
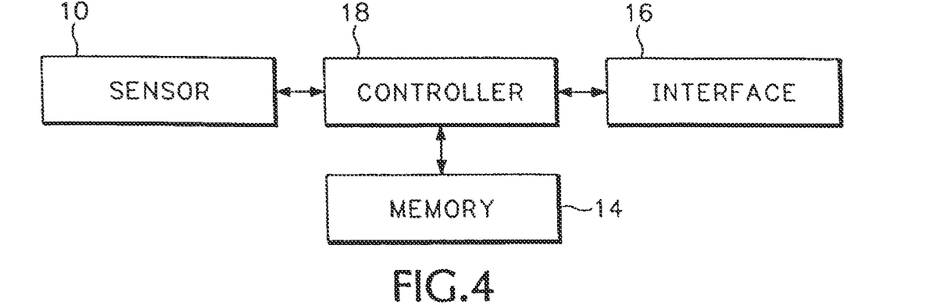
FIG. 4 is a block diagram showing a second preferred embodiment of athletic performance measurement device according to the present invention.

Another preferred embodiment of an athletic performance measurement device 10 is shown in FIG. 4. As with the previously discussed embodiment, this embodiment includes a sensor 12, a memory 14, and an interface 16. This embodiment additionally includes a controller 18, however, for controlling the transfer of data between the sensor 12, the memory 14, and the interface 16. Further, with this embodiment, the memory 14 has a read-only portion (ROM) and a read-write portion (RAM). The read-only portion stores operation instructions for the controller 18 and the read-write portion stores the athletic performance information measured by the sensor 12.

Further, while the interface 16 may continue to be a passive radio frequency transmitter, the controller 18 allows for more complex interfaces. For example, in one embodiment of the invention, the interface 16 is a data port, such as a serial data port or a parallel data port. The interface 16 may alternately include an active radio transmitter, or an infrared transmitter, or any combination of interface devices. A number of interfaces, including a variety of data ports, radio transmitters, and infrared transmitters, are well known in the art, and can be constructed and employed by those of ordinary skill in the art.

The controller 18 also allows for a more complex sensor. As before, the sensor 12 can be an impact sensor and an accelerometer. The sensor 12 may also be, for example, a device for measuring pulse rate, distance traveled, calories burned, or any other known sensor for measuring a standard of athletic performance. In still other embodiments, the controller 18 performs calculations upon the measured athletic performance information, to generate additional athletic performance information (e.g., average pulse rate, average speed, etc.).

For some preferred embodiments, this athletic performance measurement device 10 is portable, and can be worn by the athlete during his athletic activity For example, in one preferred embodiment, the athletic performance measurement device 10 is encapsulated in a portable module that can be removably attached to the athlete's article of footwear, such as his shoe. Such portable modules are well known, and are commonly employed in, for example, foot races such as marathons.

With other preferred embodiments, the athlete wears the athletic performance measurement device 10 on his wrist, either by itself or as a component of a wristwatch. Wrist-worn performance measuring devices, such as pulse meters and pedometers, are well known. In still other embodiments of the invention, the athletic performance measurement device is hand-held during the athletic activity.

Figure 5:
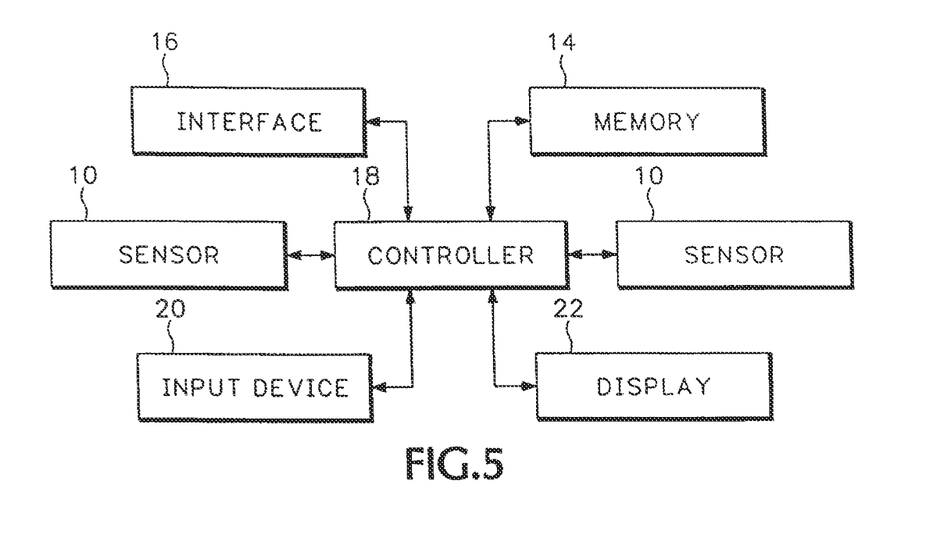
FIG. 5 is a block diagram showing a third preferred embodiment of an athletic performance measurement device according to the present invention.

Yet another embodiment of the invention is shown in FIG. 5. In this embodiment, the athletic performance measurement device 10 includes the sensor 12, controller 18, memory 14 and interface 16 of the previous embodiment. It further includes an additional sensor 12, an input device 20, and a display 22. The display 22 allows the athlete to see his own measured athletic performance information, either at the end of his athletic activity, during his athletic activity, or both.

The input device 20 also allows the athlete to use the athletic performance measurement device 10 in a variety of ways. For example, the same athletic performance measurement device 10 can be used by more than one person. That is, by using the input device, different athletes can personalize the gathered athletic performance information.

Thus, two or more friends can share a single athletic performance measurement device 10. When the first friend uses the device, he operates the input device 20 to input a code specific to him. This code then instructs the athletic performance measurement device 10 to store the subsequently gathered performance information in a particular memory location, or with a memory label identifying the athletic performance information as his. When the second friend uses the athletic performance measurement device, he uses the input to enter a different code, instructing the athletic performance measurement device to store the subsequently gathered performance information in a different memory location, or with a different memory label.

Further, when the athletic performance measurement device 10 is part of a larger unit, e.g., a wristwatch, then the input device 20 can be used to activate or deactivate the athletic performance measurement device 10. Moreover, the athlete can use the input device to select whether the first sensor 12, the second sensor 12, or both measure the athletic performance values.

The input device 20 is preferably a keyboard or an active surface that responds to a stylus. Such input devices are well-known, and their construction and use are well within the capability of those of ordinary skill in the art. Similarly, the display may be a liquid crystal display, a light emitting diode display, or any other type of conventionally known display.

As with the previous embodiments, this embodiment may be encapsulated in a portable module that can be removably attached to, for example, a shoe, or worn on the athlete's wrist. Further, this embodiment also may be hand-held, as with the previous embodiments.

While the use of two sensors 12 was described with reference to only the preceding embodiment, it should be noted that any embodiment of the invention, including any of the foregoing embodiments, may employ two or more sensors. Likewise, it should be noted that the display 22 and input device 20 need not be used together, but that either could be employed together or alone with any embodiment of the invention, including any of the foregoing embodiments.

Transmission of Performance Information

Once the athletic performance information has been gathered, it can be transmitted to the reward determining location 30 (e.g., an athletic shoe manufacturer) in a number of ways.

Figure 6:
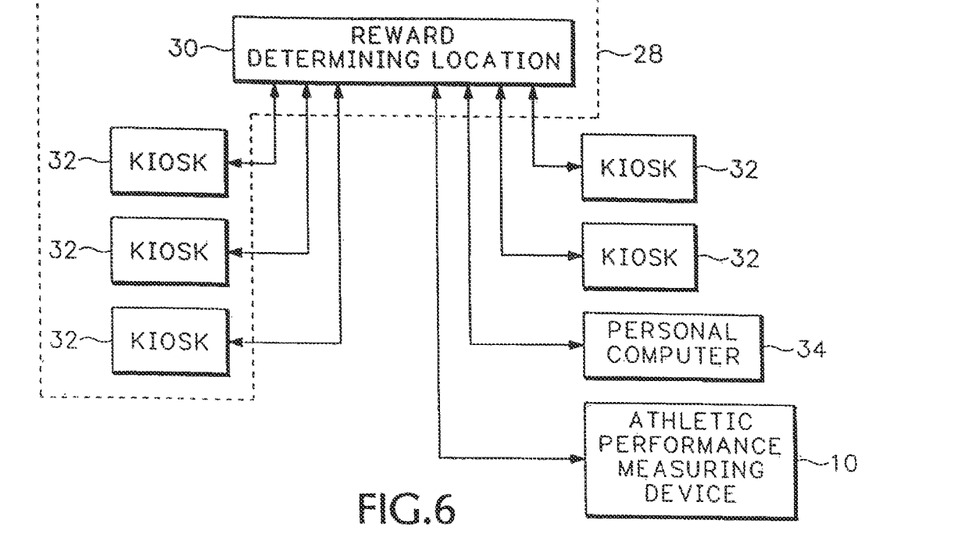
FIG. 6 illustrates two preferred embodiments for transmitting collected athletic performance information according to the present invention.

In one preferred embodiment, shown in FIG. 6, the reward determining location 30 collects the gathered athletic performance information through collection devices in a wide area network (WAN) 28. In this embodiment, the reward determination location 30 preferably maintains computer kiosks 32 at various locations, such as boutique stores or retail stores that sell its athletic equipment. Each of these computer kiosks 32 has at least one interface 16 for receiving gathered athletic performance information athletic performance measurement devices 10.

For example, the interface 16 may be a radio frequency transceiver, for obtaining athletic performance information from athletic performance measurement devices 10 that employ a radio frequency transmitter, as discussed above. The interface 16 may alternately, or additionally, have a serial or parallel data port, or in infrared transceiver. Preferably, every kiosk 32 in the network will has a sufficient variety of interfaces so as to be compatible with any athletic performance measurement device.

Each kiosk 32 also has a transmission device, such as a modem, a digital communication line, or a wireless communication unit, for transmitting the athletic activity performance information to the reward determining location. The various types of transmission devices are numerous and well-known, and thus are not described here in detail in this embodiment, the kiosk 32 can transmit collected athletic performance information immediately to the manufacturer, or postpone transmission until it collects a specific amount of athletic performance information.

In another preferred embodiment, also shown in FIG. 6, the reward determining location 30 is individually contacted by different collection devices. For example, with this embodiment, the athletic equipment manufacturer also collects athletic performance information through computer kiosks 32 it maintains at various locations. Rather than being continuously connected to the manufacturer through a communications network, however, each kiosk 32 operates as a stand-alone unit until it transmits athletic performance information to the manufacturer.

When the kiosk 32 decides to transmit the athletic performance information, it initiates a communication procedure between it and the manufacturer (e.g., a dial-up procedure with a modem). After establishing communication with the manufacturer, the kiosk then transmits its collected athletic performance information. As with the previous embodiment, the kiosk 32 can transmit collected athletic performance information immediately to the manufacturer, or postpone transmission until it collects a specific amount of athletic performance information.

As seen in FIG. 6, individual personal computers 34 can also be used as collection devices to collect and transmit gathered athletic performance information to the manufacturer. With this arrangement, the athlete gathers athletic performance information with the athletic performance measurement device, and then links the athletic performance measurement device to his personal computer 34. Any conventional linking arrangement can be employed to link the athletic performance measurement device with the personal computer 34. Such linking arrangements, like those for linking personal information management devices (e.g., the Palm Pilot™) to a personal computer, are well known, and are thus not described in detail here.

After the athletic performance measurement device 10 downloads its gathered athletic performance information into the athlete's personal computer 34, the athlete can then initiate a communication procedure between his personal computer and the manufacturer. Again, such communication procedures (e.g., a dial-up procedure with a modem) are well known in the art. After communication between the athlete's personal computer and the manufacturer is established, the collected athletic performance information is transferred from the athlete's personal computer to the manufacturer. The transfer can take place immediately after athletic performance measurement device downloads the gathered performance information to the personal computer, or at a later time selected by the athlete (e.g., after a significant amount of athletic performance information has been collected).

The above-preferred embodiments specifically employ computers. The general use, operation, and construction of a computer system are known and have been disclosed in numerous patents, such as U.S. Pat. No. 5,818,447 to Wolf et al. To prevent undue repetition as to these basic elements, Applicants hereby incorporate the following patents by reference: U.S. Pat. No. 5,818,447 to Wolf et al. and U.S. Pat. No. 5,752,025 to Shakib et al.

Further, it will be understood that any suitable personal computing device can be employed to collect and transmit the gathered athletic performance information. For example, distributed programming computers (i.e., computers that do not store their own programming instructions, but receive them over a network) or personal information management computers (such as the Palm Pilot™) can be alternately employed.

For still other embodiments of the invention, athletic performance measurement device is configured to download its gathered athletic performance information directly to the manufacturer. For example, according to one embodiment of the invention, the athletic performance measurement device 10 contains a modem. The modem (which can be for either hard-line communication or can be for wireless communication) is used to establish direct communication between the athletic performance measurement device 10 and the manufacturer. Other embodiments employ alternate communication procedures, such as a completely digital communication line.

Figure 7:
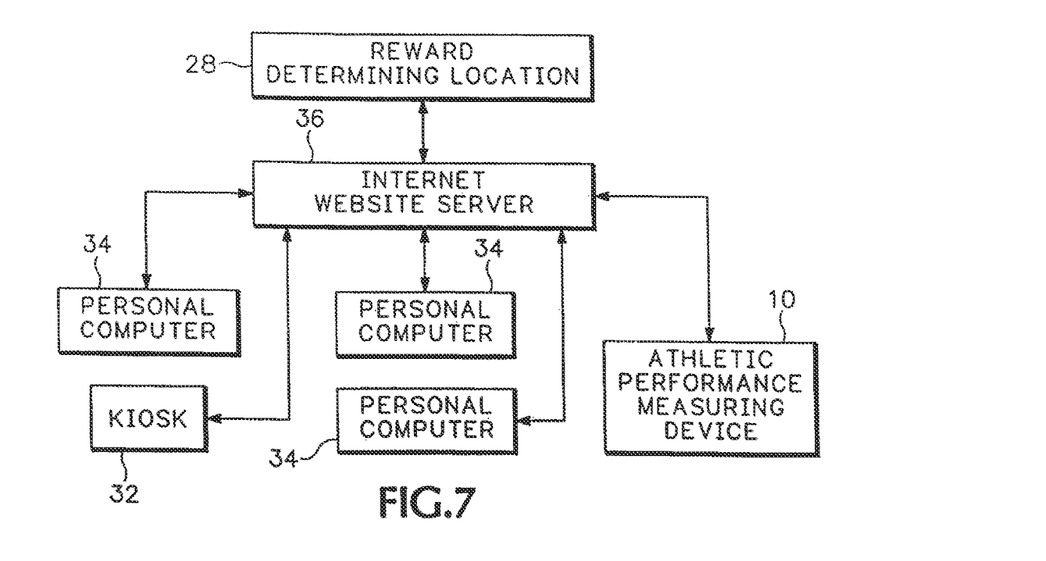
FIG. 7 illustrates a third preferred embodiment for transmitting collected athletic performance information according to the present invention.

Still another embodiment of the invention is shown in FIG. 7. In this embodiment, athletes indirectly transmit gathered athletic performance information to the manufacturer by way of an Internet website server 36. With this arrangement, the athlete links his athletic performance measurement device 10 to his personal computer 34 or other type of suitable computer device, as previously discussed. Rather than communicating over a direct line with the athletic equipment manufacturer; however, the computer device communicates with the manufacturer's Internet website server 36 through an Internet service provider.

This type of communication allows the athlete to obtain access to other information and services provided by the manufacturer when he transmits his athletic performance information. This feature is particularly advantageous when the athlete receives a purchase discount as a reward for his athletic performance. The athlete can then take immediate advantage of his reward by purchasing additional products from the manufacturer through the manufacturer's website.

As with the previous embodiment, the athletic performance measurement device may be configured to communicate directly with the Internet website server 36 through an Internet service provider. Also, the manufacturer can maintain kiosks for transmitting collected athletic performance information through an Internet website server.

Any suitable format can be used to transmit the athletic performance information to the Internet website server 36. A variety of information formats, such as the MP3 and the Microsoft Windows Media Audio formats for audio information, and the JPEG, MPEG and MPEG II formats for video information, are just examples of well known information formats that can be employed.

It should be noted that, for most embodiments of the invention, it is necessary to distinguish each athlete's performance information from that of other athletes. Thus, in addition to the athletic performance information, each athletic information collection device will also preferably transmit an identification code identifying the source of the athletic performance information.

More specifically, the identification code can be used to identify the athletic performance measuring device providing the athletic performance information. For example, when the athletic performance measuring device 10 is permanently attached to a product (e.g., embedded in a shoe), then the identification code may identify the product rather than the athlete.

Alternately, the identification code can be used to identify the athlete performing the measured athletic activity rather than a specific athletic performance measurement device. This arrangement is preferably when the athletic performance measurement device can be used by more than one athlete.

The identification code can be input by the athlete at various times. For example, according to some embodiments of the invention, the athlete inputs the identification code prior to or just after performing the athletic activity. With other embodiments of the invention, however, the athlete postpones entering the identification code until he transfers the athletic performance information to an information collection device. With yet other embodiments of the invention, the athlete enters the identification code directly into the collection device rather than the athletic performance measurement device.

According to still other embodiments, the identification code is permanently stored in the memory of the athletic performance measurement device, and automatically is transferred to the collection device or transmitted to the reward determining location with the athletic performance information. This arrangement is preferable when the identification code identifies the athletic performance measurement device rather than the athlete.

The Reward

According to the method of the invention, the person wearing the product receives rewards from the manufacturer proportional to his athletic performance and/or general use of the product. These rewards will then encourage the athlete to continue or even increase his athletic performance in order to obtain additional rewards. As will be understood, these rewards can be anything that encourages the athlete or product user.

For example, the manufacturer can provide discounts for future purchases of its athletic equipment, or even free athletic equipment. The manufacturer can also, for example, provide cash awards, or discounts or gifts of other's goods or services. These rewards could be accrued over time, awarded immediately, or awarded on any basis desired by the manufacturer.

Additionally, as briefly noted above, the manufacturer can provide authorized requestors with their own performance information or the performance information of other athletes. This is useful, for example, for an athlete's coach or doctor who needs a record of the athlete's performance.

The athlete also can use his collected performance information as a detailed record of his own use. Thus, an athlete can use the collected performance information to track the changes in his own athletic performance over time. This feature is particularly useful in conjunction with an Internet website. The website allows an authorized user to readily obtain the desired information from any personal computer, without having to initiate a communication procedure specific to the manufacturer or traveling to a fixed computer kiosk.

As also previously noted, the manufacturer can "reward" the athlete by providing the athlete, or any other authorized requestor, with information comparing the athlete's performance to the athletic performance of other athletes. Thus, for example, an athlete can compare his performance with that of a friend or rival, spurring the athlete on to improve his athletic performance. This feature also is useful to a team coach or doctor, who needs to efficiently review athletic performance information for an entire team. Similarly, the compilation of performance and use data collected from numerous people wearing the product can provide invaluable information to researchers, including shoe designers, marketers, and biomedical researchers. Still further, the manufacturer can reward the athlete by comparing his performance with that of a professional athlete.

In other embodiments of the invention, the manufacturer provides additional Internet web sites to which only athletes with a certain level of rewards have access. The manufacturer can also provide games where athletes progress and succeed based upon their level of athletic performance. These games can be individual games, or games where athletes compete interactively against each other. Additional rewards will of course be apparent to those of ordinary skill in the art, and it is intended that these be encompassed by the scope of the appended claims.

With the above-described embodiments, the rewards are calculated by the reward determining location (e.g., the product manufacturer). However, it should be noted that alternate embodiments of the invention calculate the rewards internally though software installed on the collection device or in the athletic performance measurement device itself. The information relating to the reward is then transferred to the reward determining location with the athletic performance information. In these embodiments, the reward determining location verifies the previously calculated reward.

Other Embodiments of the Invention

In addition to those embodiments discussed above that specifically measure and reward athletic performance, it will be apparent that the method of the invention can be employed to measure and encourage the general, non-athletic, use of any product. For example, the performance measuring devices attached to the product can sense and record activity levels associated with general, non-athletic use of the product.

In one such embodiment, the method of the invention can be employed in articles of footwear to record, track, and reward general day-to-day wearing and use of the articles of footwear. In this embodiment, the method of the present invention would encourage a potential customer to buy and use the articles of footwear, but not necessarily only for fitness or athletic purposes. Similarly, use information collected from this embodiment will provide the footwear manufacturer with valuable insight into how its footwear products are actually being used by its customers.

Of course, it will be understood that the invention is not limited to use with athletic equipment, but can be applied to monitor and encourage the use of any equipment.

CONCLUSION

In view of the wide variety of embodiments to which the principles of the invention can be applied, it should be apparent that the detailed embodiments are illustrative only and should not be taken as limiting the scope of the invention. Rather, the claimed invention includes all such modifications as may come within the scope of the following claims and equivalents thereto.

What is claimed is:
1. A method, comprising:
  measuring, by a measurement device, activity information indicating performance of a physical activity by a first user, wherein the measurement device is removably attachable to a piece of athletic equipment;
  transmitting, by the measurement device, the activity information to a reward kiosk, wherein the kiosk is associated with and operatively connected to a remote reward determination location;

transmitting, by the measurement device and to the reward kiosk, an identification code identifying the measurement device;

receiving input corresponding to a user identification code that distinguishes between users of the piece of athletic equipment;

determining, by the measurement device, reward information based on the transmitted activity information, wherein the reward information comprises at least a redeemable reward;

requesting, from a computing device, information comparing the transmitted activity information with athletic activity information corresponding to a second user; and receiving the comparison information.

2. The method recited in claim 1, wherein the second user is a professional athlete.

3. The method recited in claim 1, wherein determining reward information further comprises:

determining that the activity information indicates the first user achieved a threshold physical activity level; and providing information to access a gaming environment in response to the determining that the threshold physical activity level has been achieved.

4. The method recited in claim 1, wherein the activity information includes one or more selected from the group consisting of: heart rate, steps taken, distance traveled, or rate of speed.

5. The method recited in claim 1, wherein the measurement device is removably attachable to an article of clothing.

6. The method recited in claim 1, wherein the measurement device is removably attachable to an article of footwear.

7. The method recited in claim 1, wherein the measurement device comprises a plurality of sensors.

8. The method recited in claim 7, wherein at least a first sensor of the plurality of sensors comprises an accelerometer.

9. The method recited in claim 7, further comprising:

receiving, by the measurement device, user input selecting at least a first sensor, of the plurality of sensors, to measure the activity information.

10. An apparatus removably attachable to a piece of athletic equipment, the apparatus comprising:

one or more processors; and memory storing computer readable instructions that, when executed by the one or more processors, cause the apparatus to at least:

measure activity information indicating performance of a physical activity by a first user;

transmit the activity information to a reward kiosk, wherein the kiosk is associated with and operatively connected to a remote reward determination location;

transmit, to the reward kiosk, an identification code identifying the apparatus;

receive input corresponding to a user identification code that distinguishes between users of the piece of athletic equipment;

determine reward information based on the transmitted activity information, wherein the reward information comprises at least a redeemable reward;

request, from a computing device, information comparing the transmitted activity information with athletic activity information corresponding to a second user; and receive the comparison information.

11. The apparatus recited in claim 10, wherein the computer readable instructions when executed further cause the apparatus to at least:

determine that the activity information indicates the first user achieved a threshold physical activity level; and in response to the determining that the threshold physical activity level has been achieved, provide information to access a website maintaining collected performance information of the first user.

12. The apparatus recited in claim 10, wherein the computer readable instructions when executed further cause the apparatus to at least:

determine that the activity information indicates the first user achieved a threshold physical activity level; and provide information to access to a gaming environment in response to the determining that the threshold physical activity level has been achieved.

13. The apparatus recited in claim 10, wherein the apparatus further comprises a plurality of sensors, and wherein the instructions, when executed, further cause the apparatus to:

receive user input selecting at least a first sensor, of the plurality of sensors, to measure the activity information.

14. A non-transitory computer readable medium storing instructions that, when executed, cause an apparatus to at least:

measure, by a measurement device, activity information indicating performance of a physical activity by a first user, wherein the measurement device is removably attachable to a piece of athletic equipment;

transmit, by the measurement device, the activity information to a reward kiosk, wherein the kiosk is associated with and operatively connected to a remote reward determination location;

transmit, to the reward kiosk, an identification code identifying the measurement device;

receive input corresponding to a user identification code that distinguishes between users of the piece of athletic equipment;

determine, by the measurement device, reward information based on the transmitted activity information, wherein the reward information comprises at least a redeemable reward;

request, from a computing device, information comparing the transmitted activity information with athletic activity information corresponding to a second user; and receive the comparison information.

15. The non-transitory computer readable medium recited in claim 14, wherein the measurement device comprises a plurality of sensors.

16. The non-transitory computer readable medium recited in claim 15, wherein the instructions, when executed, further cause the apparatus to receive input selecting at least one of the plurality of sensors to measure the activity information.

17. The non-transitory computer readable medium recited in claim 14, wherein the second user is a professional athlete.

18. The non-transitory computer readable medium recited in claim 14, wherein the instructions, when executed, further cause the apparatus to determine reward information by:

determining that the activity information indicates the first user achieved a threshold physical activity level; and providing information to access a gaming environment in response to the determining that the threshold physical activity level has been achieved.

19. The non-transitory computer readable medium recited in claim 14, wherein the activity information includes one or more selected from the group consisting of: heart rate, steps taken, distance traveled, or rate of speed.

20. The non-transitory computer readable medium recited in claim 14, wherein the measurement device comprises a plurality of sensors.

* * * * *